United States Patent [19]

Jolanki et al.

[11]  4,111,560

[45]  Sep. 5, 1978

[54] METHOD AND APPARATUS FOR DETERMINING A PROPERTY OF A GIVEN SUBSTANCE

[75] Inventors: Jorma Jolanki, Helsinki; Ilpo Saxelin, Perttula; Hannu Pönni, Suulisniemi, all of Finland

[73] Assignee: Insinooritoimisto Innotec Oy, Finland

[21] Appl. No.: 736,736

[22] Filed: Oct. 29, 1976

[30] Foreign Application Priority Data

Oct. 30, 1975 [FI] Finland ............................... 75 3039

[51] Int. Cl.² .......................................... G01N 21/02
[52] U.S. Cl. ............................... 356/205; 73/61.1 R; 250/565; 250/573; 356/181; 250/343
[58] Field of Search .................. 356/204, 205, 181; 250/343, 573, 565; 73/61.1 R, 61 R

[56] References Cited

U.S. PATENT DOCUMENTS

| | | | |
|---|---|---|---|
| 3,111,839 | 11/1963 | Evans et al. | 73/61 R |
| 3,200,700 | 8/1965 | Topol | 73/61 R |
| 3,743,424 | 7/1963 | Coulter | 356/181 |
| 3,892,127 | 7/1975 | Cirulis et al. | 73/61.1 R |
| 3,992,109 | 11/1976 | Bock | 356/181 |

*Primary Examiner*—John K. Corbin
*Assistant Examiner*—R. A. Rosenberger
*Attorney, Agent, or Firm*—Steinberg & Blake

[57] ABSTRACT

In order to determine a property of a given substance, the latter and a reference substance are alternately fed, by a suitable pump, for example, into and through a receiver in which each substance remains for a given time increment before the other substance is delivered thereto. The receiver is permeable to predetermined radiation which travels through the receiver and the substance therein to be absorbed to different extents by the given substance and the reference substance. The radiation travelling beyond the receiver is measured to derive therefrom alternate measurements resulting from the radiation travelling through the given substance and the radiation travelling through the reference substance, this radiation being derived from a suitable source which directs the radiation through the receiver and the substance therein. These alternate measurements are compared to determine the property of the given substance.

9 Claims, 3 Drawing Figures

METHOD AND APPARATUS FOR DETERMINING A PROPERTY OF A GIVEN SUBSTANCE

BACKGROUND OF THE INVENTION

The present invention relates to methods and apparatus for determining properties of given substances.

The invention relates to that type of method and apparatus which utilizes IR (infrared) spectroscopy by means of which it is possible to measure exceedingly small differential concentrations in various samples.

Along with the development of infrared analyzers, instruments based also upon molecular resonance absorption have already been utilized for many different purposes. Up to the present time the use of such instruments has in most cases required considerable experience inasmuch as conventional instruments of this type have components requiring numerous adjustments and zero settings. Such adjustments and settings are essential in order to achieve good results from instruments of the type referred to above.

It is common practice with such instruments to provide two measuring paths, the sample which is to be measured being situated along one of these paths while a reference substance is situated along the other of these paths, and the measurement is derived on the basis of the difference in absorption taking place along these two paths. Where radiation in the form of light, for example, is utilized, an unavoidable difficulty encountered with instruments of this type is in rendering both paths identical so that in all situations the cuvettes which receive the sample and reference substances will at the instant of measurement receive identical quantities of radiation. In this connection it is to be noted that in addition to providing identical quantities of radiation it is also essential to maintain the other operating parameters constant, and this identity of the operating conditions must be maintained under all operating variables and during aging of the instrument.

It has already been attempted to reduce the differences between the variables encountered along the two different measuring paths where the sample and reference are respectively situated, as by making these measuring paths as closely identical as possible, or mirror images of each other. However, with the continuous increase in the desire and requirement of sensitivity of the measurement, and insofar as the apparatus provides the possibility, the true problem is at the present time how to maintain the two paths mutually comparable with an extremely high degree of accuracy in spite of such factors as soiling, aging, and other sources.

In certain types of apparatus as referred to above, use is made of infrared spectroscopy with the intensity of the radiation which travels through the sample being compared with the intensity of the radiation travelling through the reference. The desired results are achieved either by comparing the measuring intensity to a constant intensity, which is obtained, for example, by covering the detector or by using a variable attenuator, by means of which the reference signal is adjusted so as to equal the measuring signal, and the position of the attenuator then indicates the amount of absorption. However, such measuring methods have their own sources of error, and it is necessary to note that the above-mentioned comparison of radiations traversing a reference cuvette and a measuring cuvette have been utilized for high-accuracy purposes. The comparison of the radiation along the different paths has been carried out by way of an interruptor frequency on the order of several hundred cycles per second, as a rule.

When it has been necessary to divide the radiation into two parts, certain drawbacks are encountered such as instability of the dividing objects, changing of the radiation pattern of the light source due to changing of the radiator temperature, for example, soiling of the sample cuvette, which evidences itself as a zero shift, changes of the mechanical dimensions of the dividing optics caused by the mechanical vibrations and ambient temperature changes and other similar causes. Elimination of these drawbacks requires frequently repeated calibration, and thus the known methods and apparatus are cumbersome for use in fields such as industrial processing.

SUMMARY OF THE INVENTION

It is thus a primary object of the present invention to provide a method and apparatus which will avoid the above drawbacks.

In particular, it is an object of the present invention to provide a method and apparatus which make it possible to measure extremely small differential concentrations.

A further object of the present invention is to provide a method and apparatus according to which it becomes possible to eliminate from the measurements sources of error such as those encountered by providing different radiation paths for a sample and a reference.

Moreover it is an object of the present invention to provide a comparison of a reference and a sample in such a way that the interruption frequency has a different order of magnitude from that which has previously been encountered with a reference and a sample respectively in different cuvettes, so that in this way it becomes possible to reduce to an appreciable extent the signal-to-noise ratio, as is easily ascertained by theoretical considerations.

Yet another object of the present invention is to correspondingly improve this signal-to-noise ratio even further, as by lengthening the integration period which is to say the time during which an average magnitude is derived from the signal. It is to be noted in this connection that the duration of the integration has, if necessary, a time required for a cuvette to have its contents changed several times.

Moreover, it is an object of the present invention to provide for the method and apparatus of the invention a highly effective manner for providing from the sample which is to be tested a reference to be compared therewith.

In addition, it is an object of the present invention to provide a method and apparatus which require only simple operations and which lend themselves to use for purposes such as industrial processing.

According to the invention a single receiving means, such as a cuvette, is provided for alternately receiving the sample and the reference substances, these being fed, as by a suitable pump means, alternately to the receiving means so as to travel therethrough while at the same time the sample and reference substances each remain at the receiving means for a predetermined interval. The receiving means is permeable to a predetermined radiation which is directed from a suitable source through the receiving means so as to be absorbed to different extents by the sample substance and reference substance which are alternately present at the receiving means. As the radiation travels beyond the receiving means it encounters a means which responds to this radiation for deriving therefrom a pair of measurements determined by the different degrees of absorption of the radiation by the sample and reference substances, and from these measurements it is possible to determine a property of the sample substance.

BRIEF DESCRIPTION OF DRAWINGS

The invention is illustrated by way of example in the accompanying drawings which form part of this application and in which.

DESCRIPTION OF PREFERRED EMBODIMENTS

Figure 1:
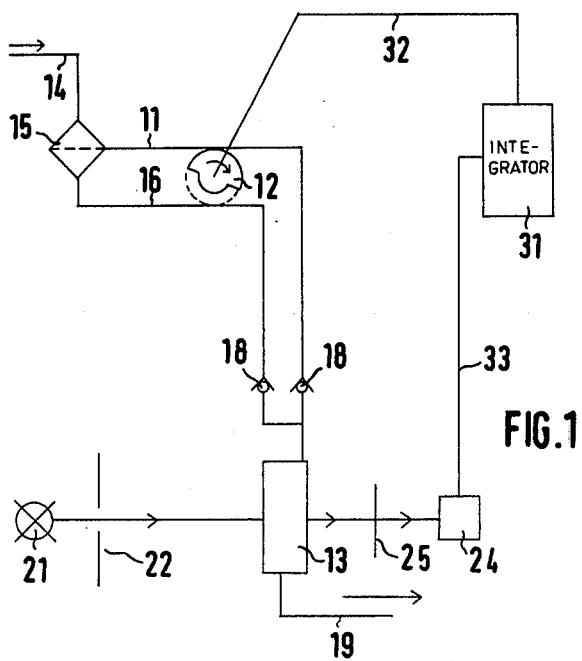
FIG. 1 is a schematic illustration of one possible method and apparatus according to the invention.

FIG. 1 schematically illustrates the arrangement of one possible measuring instrument according to the invention, FIG. 1 showing a feed means which includes the schematically illustrated pump 12, by means of which a measuring sample and a reference sample are alternately fed into the cuvette 13, utilizing components such as valves 18 of a suitable type so as to prevent reverse flow. The components associated with the optical path in FIG. 1 have been shown only schematically inasmuch as these components are familiar to any person skilled in the art.

Figure 2:
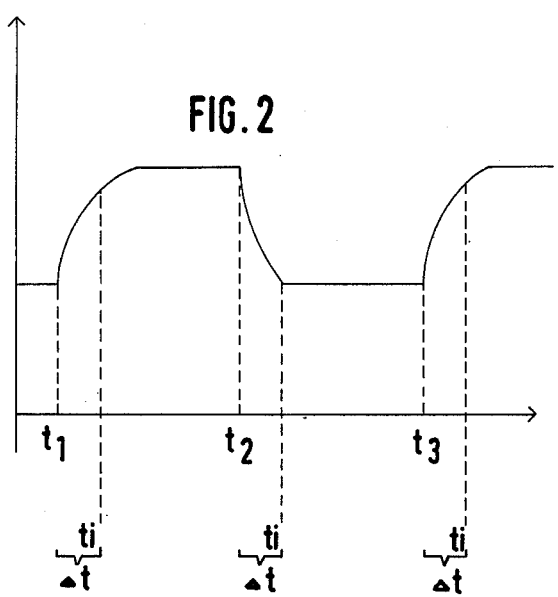
FIG. 2 is a graph illustrating variation of voltage with respect to time, demonstrating the operation of the method and apparatus of the invention.

The graph of FIG. 2 shows variations in the course of time of voltage derived from a detector, FIG. 2 also showing the time periodicity, or cycling, forming the basis of integration.

In FIG. 1 the sample substance which is to be examined so as to determine a property thereof enters the instrument through the feed tube 11 while the reference substance enters through the tube 16. The measurement is carried out as a comparison of the absorption produced by the sample substance and that produced by the reference substance. The tubes 11 and 16 are respectively provided with non-return check valves 18 or the equivalent thereof, these valves being situated immediately upstream of the cuvette 13 which forms a receiving means for alternately receiving both the sample substance and the reference substance. By situating the valves 18 immediately before the cuvette 13, the differential pressures which may be present in the tubes will not cause any mixing of the substances before their entrance into the cuvette. In the event that the substances which are handled are liquids and the tubes have rigid walls, it is sufficient if a pair of feed pumps are respectively provided to pump the liquids through these tubes and, with these feed pumps each provided with their own check valves. Both the sample substance and the reference substance are fed into the cuvette by the use of the pump means 12, or a pair of pumps may be provided to operate alternately at the pair of tubes, respectively. The capacity of the pump means and its other properties are determined in accordance with the size of the cuvette which is utilized and in accordance with the desired frequency of alternation between the sample and reference substances. By way of the cycling of the pump or the pair of pumps, it is also possible to control the indicating signal from the sole detector of the measuring instrument so that the indicating signal will clearly indicate either measurement of the reference substance or measurement of the sample substance. The required control for this purpose is indicated by the conductor 32.

While the sample and reference substances may be derived from any suitable sources, a preferred derivation of these substances, in accordance with a further feature of the invention, resides in feeding only the sample substance through the tube or pipe 14 into a filter means 15. The filter means 15 operates in such a way that it filters from the sample substance only that component which serves as the basis of examination of the sample substance so as to determine a given property thereof.' Thus at the filter means 15 the sample substance is divided into two parts, one of which is a non-filtered substance corresponding to the sample substance and the other of which is a filtered substance which forms the reference substance, the sample and reference substances being respectively delivered to the tubes 11 and 16 from the filter means 15. In this way the reference substance delivered to the tube 16 does not contain any appreciable amount of that component which gives to the sample substance the property which is to be measured. At the same time, in the sample substance which flows through the tube 11, this substance which constitutes the object of measurement is, if required, concentrated in the transporting base substance. Thus, it is possible, for example, to measure the oil content of water, and this can be accomplished by separating by use of an ultra-filter all of the oil from the fluid which reaches the reference substance tube 16, while all of the other factors such as the varying saline content of the water remain the same in both of the tubes 11 and 16. In this way these other factors will have no influence on the result of the measurement. After travelling through the receiving means which is formed by the cuvette 13, the substances are received in a suitable drain pipe or tube 19.

The spectrometer part of the measuring instrument is illustrated in FIG. 1 in a highly schematic manner because the details of this part of the instrument do not affect the possibilities of utilizing the invention. Thus, the receiving means formed by the cuvette 13 is of course permeable to a predetermined radiation derived from the illustrated lamp 21 or any other suitable radiation source. The radiation from the source 21 travels through an aperture, limiting stop, or diaphragm 22 so that a precisely determined beam of radiation reaches the receiving means 13 to travel therethrough as well as through the particular substance therein. As the radiation passes through the cuvette 13, the radiation is attenuated depending upon the absorption properties of the particular substance which is in the cuvette. The radiation when travelling beyond the cuvette 13 reaches a detector 24 of a means for measuring the different radiations resulting from the different degrees of absorption by the sample and reference substances. However, before reaching the detector 24, the radiation passes through a suitable filter 25. The location of the filter 25 may be freely chosen so as to achieve the best possible result, considering the operation of the instrument.

From the detector 24 an electrical signal indicating the amount of incident radiation is conducted to an integrator 31 of the instrument by way of the conductor 33, this integrator 31 of course being controlled by way of the conductor 32, in accordance with the particular stage and the pumping cycle of the pump 12, so that the integrator 31 will properly respond to the sample or reference substance which at any given instant happens to be in the receiving means 13. The integrator 31 will comprise separate integration components for the time integral of the radiation that has passed through the sample substance and for the time integral of the radiation traversing the reference substance. These separate integration components are of course controlled by way of the conductor 32 so as to be operative in such a way that the components for integrating radiation after absorption by the sample substance are rendered operative while the sample substance is in the cuvette 13 while the components for integrating radiation resulting from absorption by the reference substance are rendered operative during the time when a reference substance is in the cuvette 13.

The results of these integration operations and the configuration of the curve to be integrated are illustrated in FIG. 2.

The pump 12 has only been shown in a highly schematic manner in FIG. 1. It is to be noted that the cam shown in FIG. 1 is rotated by the pump so as to show that the pumping takes place with a cam control having a 180° phase shift with respect to the pair of tubes 11 and 16.

Figure 3:
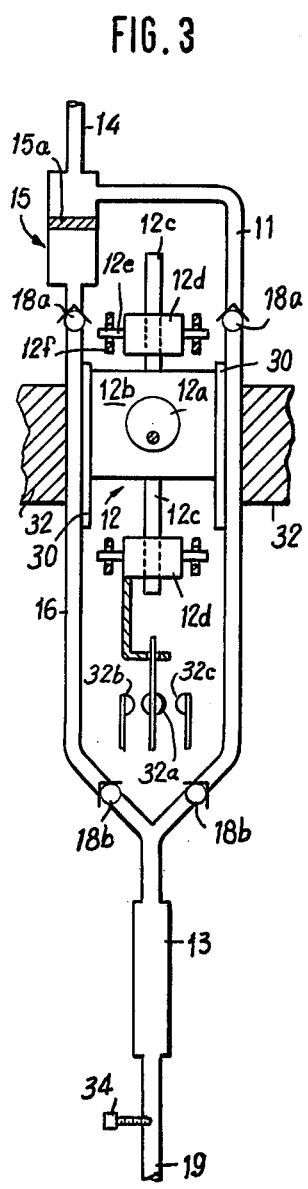
FIG. 3 is a schematic illustration of part of the system of FIG. 1 illustrating details of a specific structure.

A suitable structure is illustrated in more detail in FIG. 3. Thus, the substance is delivered through the pipe 14 to the illustrated filter means 15 which has a filtering component 15a, which is schematically illustrated. Beyond the filtering component 15a, the reference substance is received by the tube 16 which in this case is flexible and elastic so that it can be compressed and will automatically expand. The substance which does not pass through the filtering component 15a is received by the tube 11 which may be made of the same material and size as the tube 16.

In the example shown in FIG. 3 each of the tubes 11 and 16 has a pair of check valves 18a and 18b arranged as illustrated, and between these check valves the tubes 11 and 16 respectively engage a pair of stationary blocks 32. Also between the check valves 18a and 18b of each of the tubes 11 and 16 there is opposed to each block 32 an elongated bar 30, and between the bars 30 it is possible for the block 12b of the pump means 12 to slidably reciprocate. These slide bars 30 are shiftable toward and away from the blocks 32. The slidable pumping block 12b is formed with a circular aperture receiving a rotary eccentric 12a of the pump means 12 so that by rotating this eccentric at a suitable speed the pair of tubes 11 and 16 will be alternately compressed and expanded. The block 12b has a pair of pins 12c respectively guided through sleeves 12d which in turn carry pins 12e guided through suitable guides 12f. In this way when the tube 16 is compressed to deliver the reference substance through and beyond the valve 18b of the tubes 16, the tube 11 expands between its check valves to suck additional sample substance into the space between the valves 18a and 18b of the tube 11. Then when the latter tube is compressed to deliver the sample substance through and beyond the check valve 18b of tube 11, the tube 16 expands to suck additional reference substance into the tube 16.

In this way the sample and reference substances are alternately delivered to the cuvette 13 which is schematically shown in FIG. 3. Also FIG. 3 shows that the drain 19 is provided with a suitable adjustable throttle 34 which controls the rate of flow.

Furthermore, the lower guide sleeve 12d is shown as having an extension operatively engaging a switch element 32a which when the block 12b is shifted toward the left, as viewed in FIG. 3, makes contact with a switch component 32b, while when the block 12b is shifted toward the right, as viewed in FIG. 3, the switch 32a makes contact with the switch element 32c. Thus the closing of the circuits through the switch elements 32b and 32c will have a timed relationship with the operation of the pump means 12 and can thus be utilized for controlling the components of the integrator 31 in the manner described above.

As a result of experiments carried out with a method and apparatus as described above, it has been found sufficient to provide a frequency of alternation between the sample and reference substances on the order of about 2 cycles per second, so that the pump means 12 is capable of pumping within ¼ sec. through the cuvette 13 a quantity of the reference or sample substance which is considerably in excess of the capacity of the cuvette. Thus, during an interval on the order of approximately one second there will be two complete alternations of the sample and reference substances. Each cycle of course includes an interval during which the two substances are each situated in the cuvette 13 during a time increment on the order of ¼ sec. Thus one complete cycle involves an interval on the order of ½ sec. In this way the substance within the cuvette is changed rapidly during each cycle.

FIG. 2 illustrates the change of radiation intensity observed by the detector 24 of the measuring means, or in other words FIG. 2 may be considered as illustrating the detector signal plotted according to time. Thus the ordinate of FIG. 2 represents voltage while the abscissa represents time. In FIG. 2 the pumping is changed from the tube 16 to the tube 11 or from the tube 11 to the tube 16 at the times $t_1$, $t_2$, $t_3$, etc. as indicated in FIG. 2. After each instant of change of the pump from one to the other of the tubes one of the two substances alternately received by the cuvette is rapidly delivered thereto while the other is rapidly discharged therefrom. Thus, the contents of the cuvette are rapidly changed. However, during the interval from one instant of change to the next instant of change, an equilibrium condition is achieved in the cuvette, this being a favorable condition at which the entire contents of the cuvette have been changed as is readily apparent from FIG. 2. Thus, referring to FIG. 2, during the time interval between the instants $t_1$ and $t_2$, the reference substance is introduced into the cuvette with the equilibrium condition being reached approximately during the interval $t_1$, which may be considered as representing a time-changing interval $\Delta t$, and between this changing interval and the time $t_2$, substantial equilibrium remains to provide the radiation measurement indicated. Then at the time $t_2$ the sample substance is introduced with equilibrium again being reached during a similar interval $t_i$ representing the changing interval $\Delta t$, and a second equilibrium condition is reached and remains until the time $t_3$ whereupon these operations are repeated. Thus during this second interval of each cycle as represented by FIG. 2 a lesser radiation resulting from greater absorption provides a lesser voltage which can be measured. Thus, with these differences in the absorptions of the sample and reference substances, suitable signals are transmitted by the conductor 33 to the integrator 31. The concentration difference consistent with this variation is found by calibrating the apparatus according to procedures known in the art from operation of other analyzers, for example by using calibration samples of known concentrations.

Of course, the operation of the integrator 31 is synchronized with the times $t_1$, $t_2$, $t_3$, in the manner described above. This of course does not mean that it is essential that the instant of integration be switched over from one integrator component to the other necessarily in coincidence with the change-over times $t_1$, $t_2$, etc. The integration change-over points should instead be selected so as to achieve the best possible end results. The change-over points of the operation of the different integrator components may be set so as to coincide, for example, with the instants $t_i$ shown in FIG. 2. It is also possible in connection with the change-over to leave an unused operating intervals increments of time of a suitable length such as the time increments $\Delta t$ indicated in FIG. 2. During these non-operating intervals the signal which is derived from the detector is not integrated. However, the integration integrals are fixed with respect to the sample and reference alternating frequency as by using a counter indicating the position of the pump means. This control is derived by the conductor 32 shown in FIG. 1.

Where the integrator components have a high enough integration time constant, the signal/noise ratio can be rendered extremely favorable. This cancels any detrimental effect exerted on this ratio by the comparatively low alternating frequency of the electronic components.

Thus, it is possible to improve to a certain extent the signal-to-noise ratio, with this ratio being correspondingly improved further by lengthening the integration, which is to say the time during which from the signal a given average magnitude is indicated. It is to be noted that the duration of the integration has, if required, a time corresponding to several cuvette-content changing cycles.

By way of the instrument of the invention a simple design and construction is achieved in a highly advantageous manner. There is no division of radiation into two parts, and there is no requirement of mechanical interruption by means of which the comparison of operations in different paths is implemented. It will be noted that the soiling of the cuvette has no effect because the influence of the soiling is the same both for the sample and for the reference substance. Furthermore, slow changes of mechanical dimensions will have no effect on the result.

The capacity of the performance of the measuring detectors has improved at the present time to such a degree that it is conceivable to measure differences of transmission on the order of $\Delta T/T' \sim 1 \cdot 10^{-5}$. Thus an exceedingly difficult problem has been encountered with respect to maintaining light paths constant through prolonged periods with such a high degree of accuracy. However, such accuracy can be achieved by way of the present invention. Light has been referred to as the radiation only as an example in the present application inasmuch as application of the apparatus to various different purposes of measurement substantially alters certain details. A person skilled in the art, however, is able to carry out the required changes and modifications implied by the particular use which is to be made with the method and apparatus of the invention.

While the invention has been illustrated by way of the specific features referred to above, it is to be noted that these details can be varied widely within the scope of the invention. For example, the mode in which the sample and reference substances are supplied does not in itself influence the invention. Only one possibility has been illustrated, for example, by utilizing an ultra-filter when it is desired to measure the quantity of oil present in water.

What is claimed is:

1. In an instrument for measuring a property of a given substance by comparing the latter with a reference substance, a single receiving means for receiving both the given substance and the reference substance, said receiving means being permeable to predetermined radiation capable of travelling through said receiving means and the substance therein to be absorbed to different degrees by the given substance and the reference substance, means for directing said predetermined radiation through said receiving means and a substance therein to be absorbed by the latter substance and to travel beyond said receiving means, feed means for feeding the given substance and the reference substance alternately through said receiving means while maintaining the reference substance and given substance in the receiving means for given time increments during which said predetermined radiation travels through and beyond said receiving means, and radiation-responsive mpans situated in part in the path of travel of said radiation beyond said receiving means for responding to said radiation to provide alternate measurements of the radiation resulting from said given substance and the radiation resulting from said reference substance and for providing from the difference between a number of said alternate measurements which follow each other sequentially through a plurality of cycles a determination of said property of said given substance, said feed means being operatively connected with said radiation-responsive means for automatically controlling the latter to change between a pair of different measuring conditions in one of which said radiation-responsive means measures radiation resulting from said reference substance and in the other of which said radiation-responsive means measures radiation resulting from said given substance.

2. The combination of claim 1 and wherein said feed means includes a pump means for pumping said substances alternately through said receiving means.

3. The combination of claim 1 and wherein a filter means receives said given substance for filtering therefrom a component thereof which provides said given substance with the property which is to be measured, to derive from said given substance a filtered substance forming said reference substance and a non-filtered substance forming said given substance, said feed means alternately feeding said filtered and non-filtered substances to said receiving means.

4. The combination of claim 3 and wherein said feed means includes along paths of travel of said filtered and non-filtered substances to said receiving means from said filter means, a pump means for alternately pumping the filtered and non-filtered substances to said receiving means.

5. In a method for measuring a property of a given substance, the steps of cyclically feeding said given substance and a reference substance alternately during each of a series of uninterrupted sequential cycles through a receiving means which is permeable to predetermined radiation, while maintaining each of said substances for a given time increment during each cycle in said receiving means, directing said predetermined radiation through and beyond said receiving means so that the radiation will be absorbed to different extents by said given substance and reference substance, deriving from the radiation travelling beyond said receiving means alternate measurements of the radiation resulting from travel of the predetermined radiation through the given substance during each of a series of said cycles and through the reference substance during each of said series of cycles, and determining the difference between the radiation measurements of said given substance during said cycles, on the one hand, and the radiation measurements of said reference substance during said cycles, on the other hand, to indicate said property.

6. In a method as recited in claim 5 and including the step of filtering the given substance to remove therefrom a component which is determinative of said property, to achieve filtered and non-filtered substances, and utilizing said filtered substance as said reference substance while utilizing the non-filtered substance as said given substance.

7. In a method as recited in claim 5 and wherein the alternate measurements of the radiation resulting from travel of the radiation through the given and reference substances is carried out repeatedly, one after the other, a number of times sufficient to achieve a favorable signal/noise ratio.

8. In a method as recited in claim 5 and wherein each substance is maintained in said receiving means for a time increment on the order of ¼ sec., so that one cycle of said substances alternating through said receiving means will be on the order of ½ sec. with two cycles of alternation of said given and reference substances being carried out on the order of each second.

9. In a method as recited in claim 5, and including the step of utilizing the change between the feeding of said given substance and the feeding of said reference substance alternately through said receiving means for controlling the radiation measurements of said given and reference substances.

* * * * *